(12) United States Patent
Wiemker et al.

(10) Patent No.: US 6,373,918 B1
(45) Date of Patent: Apr. 16, 2002

(54) METHOD FOR THE DETECTION OF CONTOURS IN AN X-RAY IMAGE

(75) Inventors: Rafael Wiemker, Kisdorf; Sabine Dippel, Hamburg; Thorsten Buzug, Kiel; Martin Stahl, Kaltenkirchen; Thomas Blaffert, Hamburg, all of (DE)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/526,429

(22) Filed: Mar. 15, 2000

(30) Foreign Application Priority Data

Mar. 16, 1999 (DE) .......................... 199 11 587
Apr. 14, 1999 (DE) .......................... 199 16 821

(51) Int. Cl.[7] ........................................... G01N 23/083
(52) U.S. Cl. .............................................. 378/62; 378/4
(58) Field of Search ........................... 378/4, 62, 98.7, 378/160

(56) References Cited

U.S. PATENT DOCUMENTS 5,054,044 A * 10/1991 Audon et al. .................. 378/91
5,081,580 A    1/1992 Takeo .......................... 250/582
5,651,042 A    7/1997 Dewaele ....................... 378/62

FOREIGN PATENT DOCUMENTS

EP    1 037 166 A1 *   9/2000

* cited by examiner

Primary Examiner—David V. Bruce

(57) ABSTRACT

The present invention relates to a method for automatically detecting contours of, for example, shutters or implants in an X-ray image. A number of closed paths is derived from the X-ray image, one of said closed paths being selected, in dependence on the contrast along the closed paths, as the contour. The closed paths may be derived from a set of line candidates on which contour pixel candidates are situated. The contour pixel candidates can be derived from a high-pass or gradient version of the X-ray image.

14 Claims, 7 Drawing Sheets

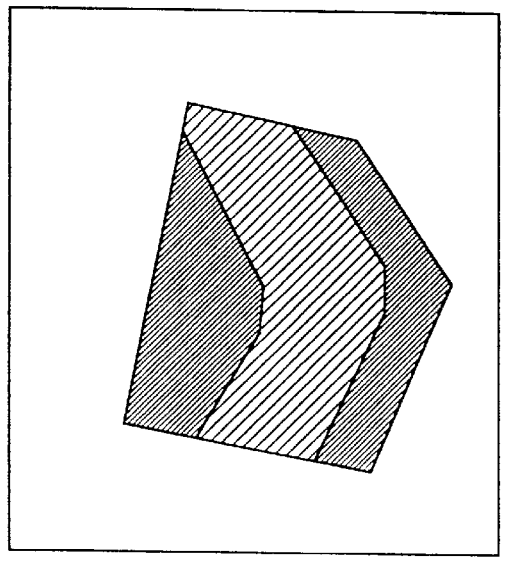 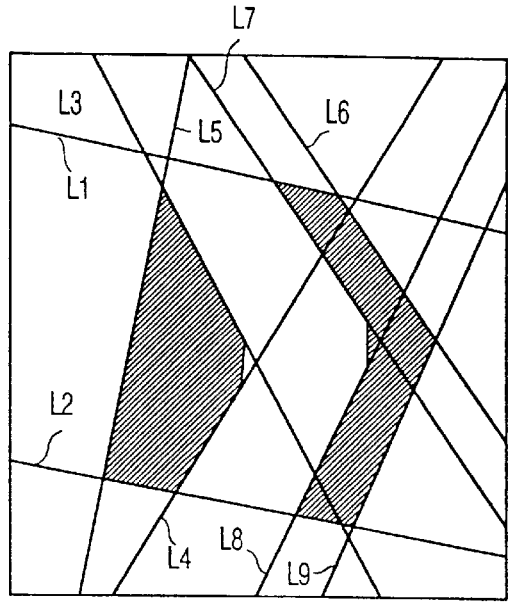
FIG. 3A  FIG. 3B
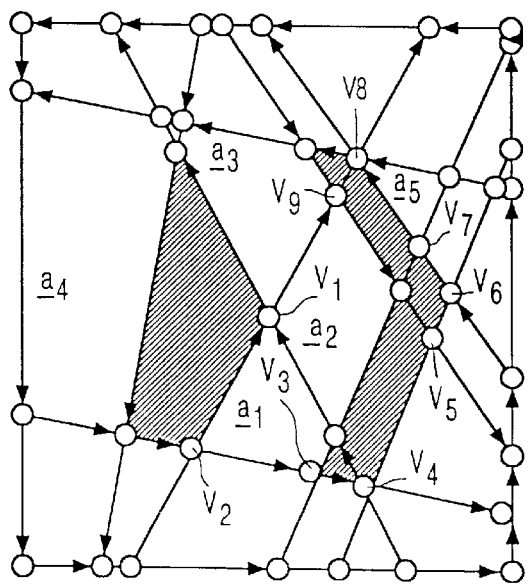 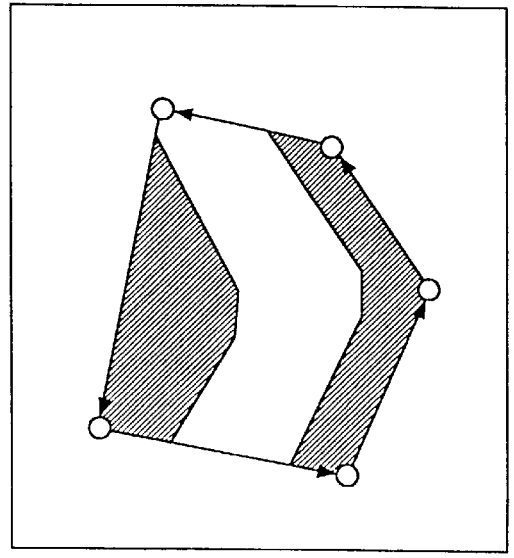
FIG. 4A  FIG. 4B

|   | $V_1$ | $V_2$ | $V_3$ | $V_4$ | $V_5$ | $V_6$ | $V_7$ | $V_8$ | $V_9$ |
|---|---|---|---|---|---|---|---|---|---|
| $V_1$ |   |   |   |   |   |   |   | × | $u_{19}$ |
| $V_2$ | $u_{21}$ |   | $u_{23}$ | × |   |   |   |   |   |
| $V_3$ |   |   |   | $u_{34}$ |   |   |   |   |   |
| $V_4$ |   |   |   |   | $u_{45}$ | × |   |   |   |
| $V_5$ |   |   |   |   |   | $u_{56}$ |   |   |   |
| $V_6$ |   |   |   |   |   |   | $u_{67}$ | × |   |
| $V_7$ |   |   | × |   |   |   |   | $u_{78}$ |   |
| $V_8$ |   |   |   |   |   |   |   |   |   |
| $V_9$ |   |   |   |   | × |   |   | $u_{98}$ |   |
| ⋮ |   |   |   |   |   |   |   |   |   |

METHOD FOR THE DETECTION OF CONTOURS IN AN X-RAY IMAGE

BACKGROUND OF THE INVENTION

1. Field of the Invention

The invention relates to a method for automatically detecting the contours of structures having a high X-ray absorption in an X-ray image. The invention also relates to an X-ray apparatus for carrying out such a method.

2. Description of Related Art

In radiological practice there are a variety of structures with a high X-ray absorption whose contours must be detected so as to enable optimum processing of the X-ray image:

1. The contours of the shutters whereby the X-ray beam striking a patient in the examination zone is restricted. Exact knowledge of the orientation in space of the shutter contours in an X-ray image can be used in various ways:
   a) The dynamic range of a monitor or a so-called hardcopy unit can be automatically adapted to the image section enclosed by the shutter contours in such a manner that the contrasts are optimally reproduced (so-called auto ranging).
   b) Upon output of an X-ray image, the region covered by the shutters can be reproduced in black or in color. If this step is not taken, these parts of the image would be very bright and could dazzle the observer.
   c) The images can be rotated and, in the case of oblique projection, corrected so that the shutter contours extend horizontally and vertically in the image reproduced. Moreover, a plurality of images can be arranged adjacent to one another in such a manner that the surface area available on a monitor or a hardcopy is optimally used.
   d) The image processing methods to be applied to the X-ray image can be limited to the section defined by the shutter contours. The amount of calculation work required for image processing can thus be significantly reduced.
2. The contours of implants in an X-ray image, for example of an artificial hip, Such implants have an X-ray absorption which is greater than that of bones but less than that of the X-ray diaphragm. The presence of such an implant in an X-ray image changes the mean gray scale value (image value) and other statistical properties of a gray scale histogram of the X-ray image. Consequently, it may happen that the automatic setting, derived from the X-ray image, of a display unit for displaying the X-ray image is not optimum. Improvements in this respect would be possible if the regions of the X-ray image in which the implant is reproduced were excluded from the histogram analysis on which the contrast setting of the display apparatus is based.

U.S. Pat. No. 5,651,042 already discloses a method for the automatic detection of shutter contours in an X-ray image wherein contour point candidates (i.e. pixels which could be situated on the contour of the shutter) are determined from the spatial variation of the image values associated with the pixels of the X-ray image (or a source image derived therefrom). The contour point candidates can be derived from a gradient image (or a high-pass image), derived from the source image, as those points for which the gradient exhibits a maximum. Using so-called linear regression, straight line candidates are calculated from such contour point candidates, which lines are arranged so that the contour point candidates lie thereon or in the immediate vicinity thereof. The line candidates may (but need not) be coincident with the shutter contours. Generally speaking, more line candidates appear as there are contours of the shutter. From these line candidates those lines are selected (4 at the most) which correspond best to one of 14 archetypes of shutter contours stored in a library. It is a prerequisite for this method that the shutter contours extend in parallel or at right angles to one another, and that the area enclosed by the shutter contours is centrally situated.

These conditions are not always satisfied in radiological practice. Even when the X-rays are confined by means of pairs of shutters extending parallel and perpendicularly to one another, the shutter contours in the X-ray image will no longer extend parallel or perpendicular to one another in the case of oblique projection. It may also occur that a part of the examination zone in which the X-ray beam is incident is covered by a lead apron or the like, the boundary of which extends parallel or perpendicular to the diaphragm edges in the X-ray image only in rare cases. The X-ray image is more likely to contain a contour which no longer coincides with a rectangle.

Moreover, digital X-ray image converters which convert the X-ray image into electric signals that can be digitized may have comparatively large dimensions (for example, 43 cm×43 cm). If, for example, only a hand or a finger is imaged by means of such an X-ray image converter, the X-ray image defined by the shutters usually will not be situated at the center but near the edge.

The same limitation holds for the method which is known from U.S. Pat. No. 5,081,680 and wherein points exhibiting a maximum gradient and situated on various straight lines through the center are determined. If more than two of such points are present on a straight line, as it will always be the case in a normal X-ray image with skeleton structures, the additional points must be excluded in a separate ranking process. The remaining points are considered to be points situated on the shutter contour, and a number of straight lines, forming a polygon, is derived from such shutter contour points by means of a Hough transformation; these lines are to represent the shutter contour.

Citation of a reference herein, or throughout this specification, is not to construed as an admission that such reference is prior art to the Applicant's invention of the invention subsequently claimed.

SUMMARY OF THE INVENTION

It is an object of the present invention to provide a method for the automatic detection of the contours of structures having a high X-ray absorption which can be reliably performed and is not restricted to given contour shapes. This object is achieved according to the invention by taking the following steps: determining a number of closed paths which serve as contour candidates in an X-ray image or an image derived therefrom, selecting, in dependence on the contrasts along the closed paths, the contour as a closed path from the number of closed paths.

Thus, according to the invention a number of closed paths is derived in the image, one of said closed paths representing the contour searched. According to the invention no individual segments of the closed paths are analyzed and rejected or confirmed, and paths having a given shape are not selected either. The underlying consideration is that along the contour particularly strong contrasts arise between the image values inside and outside the image region defined thereby. The closed path along which the strongest contrasts occur is thus selected as the contour.

A method which is particularly suitable for determining a shutter contour includes the steps of determining contour point candidates from the spatial variation of the image values associated with the pixels of the X-ray image or a source image derived therefrom, determining line candidates from the contour point candidates in such a manner that a row of contour point candidates is situated on each line candidate or immediately adjacent to such a candidate, forming closed paths as shutter contour candidates composed of segments of different line candidates, and selecting a closed path as the shutter contour in dependence on the contrasts along the closed paths. Among the contour point candidates initially derived from the source image there are a large number in clinical practice which are not situated on a shutter contour. In this version however, no attempts are made to exclude such contour point candidates from further processing from the very start. They rather serve to determine line candidates on which, or in the immediate vicinity of which, the contour point candidates are situated. Such line candidates may form, at least partly, a part of the shutter contour; however, they may also be associated with an anatomical contour in the X-ray image.

Once more no attempts are made to exclude such line candidates from the further processing. Instead, closed paths (cyclic paths) are formed, i.e. polygons, whose start coincides with the end thereof. A plurality of closed paths can be composed from the segments of different line candidates. One of these closed paths represents the shutter contour. The selection of this one path as the shutter contour is based on the consideration that along the shutter contour particularly strong contrasts occur between the image values inside and outside the image region defined thereby.

The closed paths can in principle also be determined in a manner other than that previously described, for example by determining the spatial variation of the zero-crossings after LoG filtering of the X-ray image. The version previously described, however, can reliably detect a shutter contour even when only individual segments of a contour edge exhibit a strong contrast.

A method which is suitable for determining the contour of an implant includes the steps of applying a Laplacian-of-Gaussian filter to an X-ray image or an image derived therefrom, determination of the closed paths on which the zero-crossings of the Laplacian-of-Gaussian-filtered image are situated, and selecting a closed path as the implant contour in dependence on the contrasts along the closed paths. This method functions reliably for the contour detection of implants, because such contours generally exhibit a distinct contrast relative to their surroundings along their entire circumference. The determination of the closed paths requires only a short calculation time in this version.

A particularly effective version for the detection of a shutter contour includes the summing of the contrasts at the edges to both sides of one of several closed paths and the determination of the closed path along which the sum is maximum as the shutter contour. The summing of the contrasts along the closed path can be performed by forming a contour integral ($U_{tot}$) along the closed path (s) of the direction derivative of the gradient ($\nabla I$) of the image values (I) in the direction of the path (s) in conformity with:

$$U_{tot} = \oint (n \nabla I^a) ds,$$

where n is a unit vector perpendicular to the closed path (s) and a is an exponent $\geq 1$, or by forming the integral ($V_{tot}$) of the Laplacian operator ($\Delta$) over the region (a) enclosed by the closed path in conformity with:

$$V_{tot} = \int \Delta I^b da$$

It can be demonstrated that the previous formulas are mathematically identical and can be converted one into the another.

In practice there is a multitude of combinations of segments of the line candidates which form a closed path and hence constitute shutter contour candidates. The number of such shutter contour candidates can be significantly reduced by restricting the selection to closed paths which enclose a respective region within which the image values are larger than those outside this region. In this respect it is assumed that the region enclosed by a shutter contour always exhibits image values which are higher than those in the region covered by the shutters.

A preferred possibility for the determination of the contour point candidates includes selecting as contour point candidates those points in the X-ray image or in the source image in which the image values exhibit the largest gradients. However, the contour point candidates can also be derived from a high-pass image in which the points which are clearly distinct from their neighbors are also highlighted.

A preferred possibility for determining the line candidates from the contour point candidates includes deriving the line candidates from the contour point candidates by a Hough transformation. The line candidates can also be determined in a different manner, for example by means of linear regression as described in U.S. Pat. No. 5,651,042. The Hough transformation, however, offers the advantage that a shutter contour will be recognized as a line candidate even when it is interrupted by long regions in which it shows practically no contrast in the X-ray image.

The step of adjusting a frame around the source image, such that the pixels in this frame correspond to the image values in the region masked by shutters, ensures that the method for determining the shutter contour according to the invention offers a correct result even when no shutters are used for the formation of an X-ray image or when such shutters are opened so wide that their contours are not reproduced in the X-ray image.

It has been found that the contour of an implant is distinct from the contours of anatomical structures in the X-ray image on the one hand in that its contrast is higher and on the other hand in that the course of the contour is straighter (i.e. smoother or less "irregular"). This fact is used by the method wherein a closed path is automatically selected, from the number of closed paths, as an implant contour in dependence on a straightness measure evaluating the straightness of the closed paths. Both selection criteria (contrast and straightness) can be used in combination, but it is also possible to select the implant contour on the basis of only one of the two criteria. A preferred possibility for determining the degree of straightness is based on the relation between the distance between the first pixel and the last pixel in a segment of a closed path, which includes a number of neighboring pixels, and the length of this segment.

A preferred application of the method for the automatic detection of an implant contour includes suppressing the region enclosed by the determined implant contour during a further step of automatic contrast adjustment in dependence on the content of the X-ray image.

An X-ray apparatus for carrying out the method according to the invention includes an X-ray source for generating X-rays which traverse an examination zone, a shutter device which is arranged between the X-ray source and the examination zone, an X-ray image converter for detecting the X-rays behind the examination zone and for generating a corresponding source image, and an image processing unit for the detection of the contours of the shutter device in the source image, wherein the image processing unit is arranged to carry out the processing steps of this invention, namely: determining contour point candidates from the spatial variation of the image values associated with the pixels of the X-ray image or a source image derived therefrom, determining line candidates from the contour point candidates in such a manner that a row of contour point candidates is situated on each line candidate or immediately adjacent to such a candidate, forming a number of closed paths as shutter contour candidates composed of segments of different line candidates, and selecting a closed path, from the number of closed paths, as the shutter contour in dependence on the contrasts to both sides of the closed paths.

BRIEF DESCRIPTION OF THE DRAWING

The invention will be described in detail hereinafter with reference to the drawings. Therein:

FIG. 3a shows the source image to be processed, FIG. 3b shows the line candidates derived from the source image, FIG. 4a shows a graph whose nodes are formed by the points of intersection of at least two line candidates, FIG. 4b shows the shutter contour derived therefrom.

DETAILED DESCRIPTION OF THE PREFERRED EMBODIMENT

Figure 1:
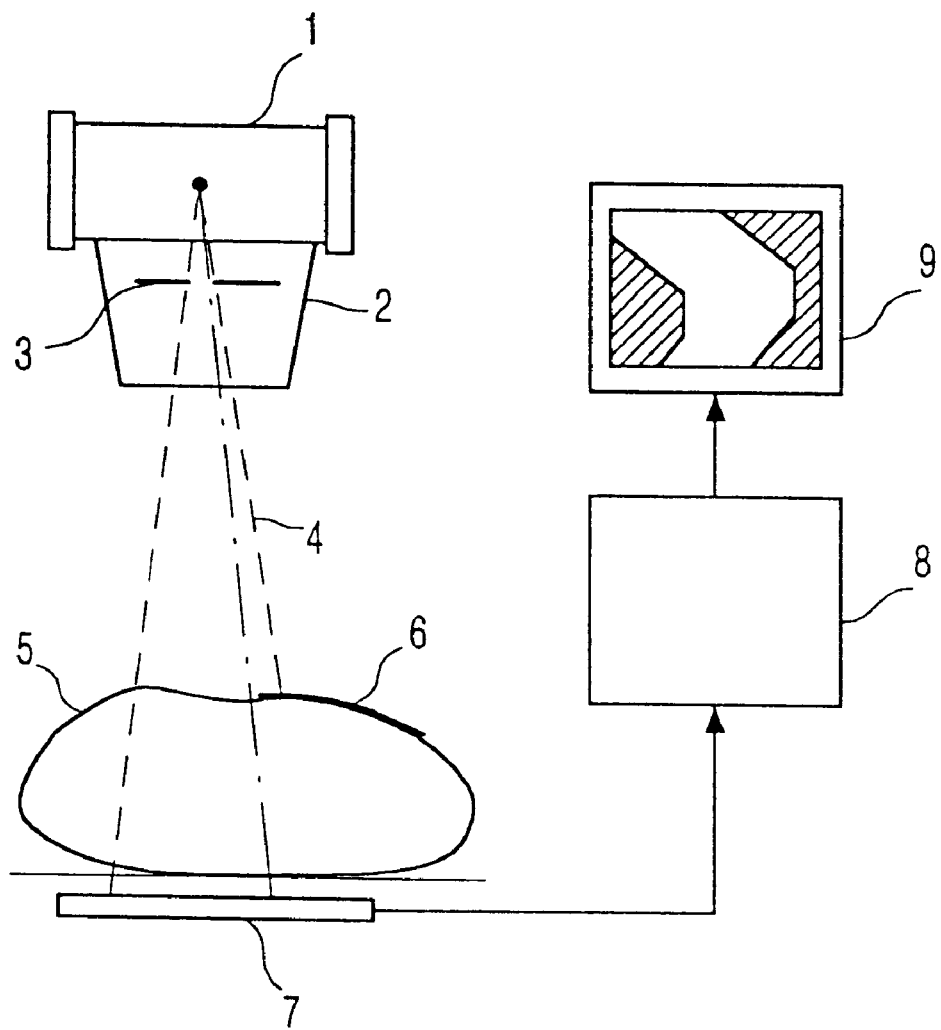
FIG. 1 shows diagrammatically an X-ray apparatus which is suitable for carrying out the invention.

The X-ray examination apparatus which is shown merely diagrammatically in FIG. 1 includes an X-ray source 1 whereto a multi-leaf collimator 2 is attached. The multi-leaf collimator includes a first pair of shutters 3 having shutter edges which extend perpendicularly to the plane of drawing and define an X-ray beam 4. The multi-leaf collimator 2 also includes (not shown) a further pair of shutters whose edges also extend horizontally but parallel to the plane of drawing of FIG. 1. The radiation beam 4 traverses an examination zone in which a patient 5 is arranged. A part of the patient can be shielded from the X-ray beam 4 by means of an appropriate cover 6 which is made of a material absorbing the X-rays, for example a lead rubber apron.

Behind the patient (viewed from the X-ray source 1) there is arranged a digital X-ray image converter which converts the X-ray image into digitized electric signals representing the X-ray image. With each pixel of the X-ray image converter there is associated an image value which is larger as the attenuation of the X-rays by the object 5 to be examined is lower. The electric signals generated by the X-ray converter 7 are acquired and further processed by an image processing unit 8. The image thus produced is displayed on a monitor 9 or output by a hardcopy unit (not shown).

Figure 2:
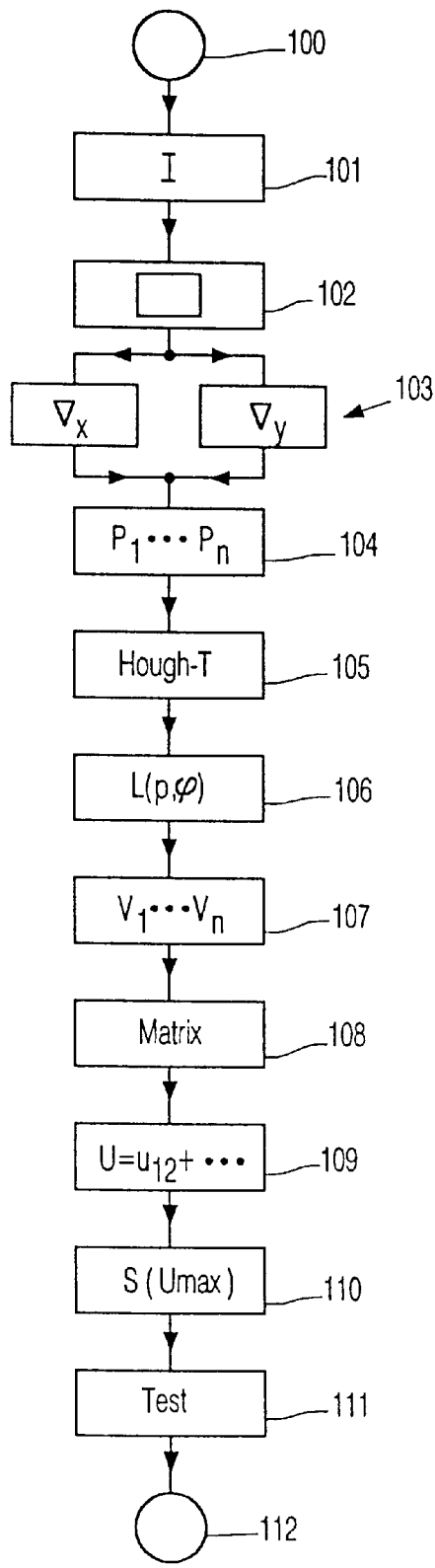
FIG. 2 shows a flow chart of the method according to the invention.

The flow chart of FIG. 2 illustrates the processing steps executed in the image processing unit 8 so as to detect the shutter contour.

After the initialization (block 100), the source image is prepared in the step 101. The preparation described hereinafter is not necessary per se, but it has been found that it is advantageous to prepare the source image supplied by the image converter 7 as follows:

The data supplied for the individual pixels is logarithmized, so that the image values are not proportional to the intensity of the X-rays behind the patient 5, but to the logarithm of this intensity. As a result, the same image impression is obtained as in the case of a conventional X-ray image on film.

The image is sub-sampled, i.e. instead of an image with for example 2000×2000 pixels, an image with for example 500×500 pixels is processed. If the degree of sub-sampling of the source image is less, more calculation work will be required whereas if the degree of sub-sampling is higher there is a risk that the shutter contour can no longer be correctly determined. The sub-sampling is accompanied by smoothing of the image values.

In the step 102 the source image (shown in FIG. 3a) is provided with a frame at its outer edges, i.e. columns and rows of pixels are added at its outer edges, the image values of said pixels being exactly equal to the image values behind a shutter. It is thus achieved that the image boundary is determined correctly even when the shutters 3 (FIG. 1) are opened so wide that they are no longer reproduced in the X-ray image.

In the step 103 two images are derived from the (prepared) source image, said two images corresponding to the x component and the y component, respectively, of the gradient of the source image. It is known that the gradient of a two-dimensional scalar field (the source image is such a scalar field I) is a vector:

$$\nabla I = (\nabla_x I, \nabla_y I) \tag{1}$$

It is known that for the vector components $\nabla_x I$ and $\nabla_y I$ it holds that:

$$\nabla_x I = \partial I / \partial x, \quad \nabla_y I = \partial I / \partial y \tag{2}$$

i.e. the vector components represent the spatial derivative of the quantity I (image values) in the x direction and the y direction, respectively. The gradient is thus determined for all pixels of the image. In order to calculate the x component of the gradient, the image is then convoluted with a one-dimensional kernel in the x direction. If the source image was suitably filtered in the step 101, the kernel may consist of the components −1, 0, +1, implying that to each pixel there is assigned the difference between the image value of the right neighbor pixel and that of the left neighbor pixel. The kernel may also be larger. However, when it is too large, inaccuracies may occur again and, moreover, the required amount of calculation work increases. The y gradient can be calculated analogously.

It has been found that it is advantageous to weight the gradient components determined for the individual pixels with the (possibly additionally spatially averaged) image value I of the relevant pixel. Weighting has the same effect as if the image values were first squared, followed by formation of the gradients in conformity with the relation:

$$\nabla I^2 = 2(I\nabla I_x, I\nabla I_y) \quad (3)$$

Weighting offers the advantage that artefacts due to the image converter are suppressed, because they become visible mainly in the masked image regions (low X-ray intensity). At the same time the shutter edges, associated with direct radiation regions in the image, are highlighted by the high image values occurring therein. Instead of $I^2$, generally speaking $I^b$ may be used, where b is a constant >0. For b=1 a pure gradient image is obtained. In the step 104 the contour point candidates are determined from the (possibly weighted) gradients determined for the individual pixels. All pixels whose gradient has an absolute value above a given threshold value are considered to be contour point candidates. The absolute value of the gradient is known to be the square root of the sum of the squares of the individual components of the gradient. Instead of such a comparatively complex arithmetic operation, however, it suffices to take into account merely the sum of the absolute values. This difference has no noticeable effects on the accuracy of the shutter contour found.

In order to determine the line candidate, a Hough transformation is performed in the next step 105, that is to say a fast Hough transformation. With each contour point having the co-ordinates x,y there is associated a line on which this point is situated and has the angle of slope $\psi$. The angle $\psi$ is calculated in conformity with the formula:

$$\psi = \arctan(\nabla_y/\nabla_x) \quad (4)$$

$\nabla_x$ and $\nabla_y$ represent the components of the gradient in the x direction and the y direction, respectively, in the relevant pixel. $\psi$ is determined in an angular range of from $-180°$ to $+180°$ in such a manner that this angle is between $-180°$ and $-90°$ when the components $\nabla_x$ and $\nabla_y$ are both negative, and between $90°$ and $180°$ when $\nabla_x$ is positive and $\nabla_y$ is negative. The distance $\rho$ between the lines through the point x,y and the co-ordinate origin is then calculated as:

$$\rho = x\cos\psi + y\sin\psi \quad (5)$$

Negative values may then also occur for $\rho$. Lines having opposed but equal values of $\rho$ are colinear and antiparallel.

Figures 5, 6:
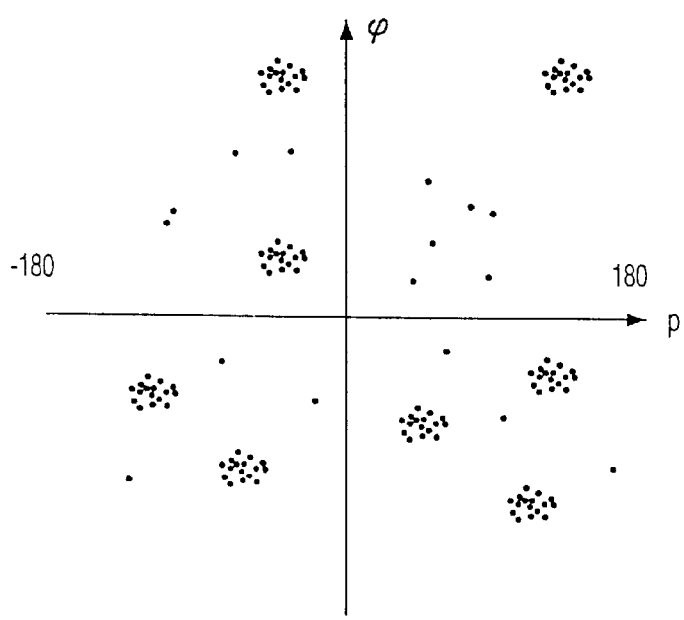
FIG. 5 shows a proximity matrix which significantly facilitates the calculation of the line integrals along different closed paths.
FIG. 6 shows a Hough matrix.

As a result of the fast Hough transformation, for each point situated in the x,y plane the content of a cell, defined by the values $\rho$ and $\psi$, in a $\rho,\psi$-matrix is incremented by 1. A typical $\rho,\psi$-matrix is shown in FIG. 6. When the contour point candidates are situated on a straight line, the content of the associated cell of the $\rho,\psi$-matrix should be incremented by the value 1 for each point on this line. Because the value $\rho,\psi$ cannot be exactly determined in practice, the entries are distributed between the cells neighboring the correct value $\rho,\psi$. Each cluster of cells with an increased entry in the $\rho,\psi$-diaphragm, therefore, corresponds to a line candidate. Thus, in the step 106 local maxima are determined in the $\rho,\psi$-matrix, each of said maxima corresponding to a line candidate.

FIG. 3b shows the line candidates L1 . . . L9, determined for the source image of FIG. 3a, in an x,y plane. They may also include the lines enclosing the outer edge. As has already been stated, an angle in the range of from $-180°$ to $+180°$ is associated with each line. Two lines with associated angles $\psi$ which deviate by $180°$ extend antiparallel to one another. A direction is thus associated with each line candidate. To the right of the line (looking in the direction of the line) there are situated pixels exposed to a lower X-ray intensity and to the left thereof there are situated pixels which were exposed to a higher radiation intensity during the X-ray exposure (this holds for the indicated one-dimensional kernel for the calculation of the gradient components $\nabla_x$ and $\nabla_y$ where the image values of the left pixel and/or the upper pixel enter with a negative weight).

In the next step 107 first the points of intersection $V_1 \ldots V_n$ of all line candidates are calculated. At least some of these points of intersection constitute corner points of the polygon defined by the shutter contour. In FIG. 4a some of these points of intersection or possible corner points are denoted by the references $V_1 \ldots V_9$. Moreover, the previously explained direction of the lines is denoted by arrows. A sequence of such corner points is called a path. When the first and the last corner point in a path coincide, the path is considered to be closed (cyclic).

For the invention it is assumed that the shutter contour is a polygon (so also a closed path) which is composed of line candidates or separate segments thereof. The invention is also based on the assumption that the contrasts along the shutter contour are maximum. Thus, the object is to find that closed path from among the multitude of possibly closed paths along which the highest possible contrast occurs. A first possibility for determining the contrast variation along a closed path consists in calculating the contour integral $U_{tot}$ in conformity with the relation $$U_{tot} = \oint (n\nabla I^b) ds \quad (6)$$

Therein, n is a vector of length 1 which always extends perpendicularly to the closed path. $U_{tot}$ thus represents the contour integral of the gradient (weighted by I) projected onto the normal to the closed path. The contour integral $U_{tot}$ can be represented as the sum of sub-integrals calculated in conformity with the relation:

$$U_{tot} = \oint \Sigma u_i \quad (7)$$

In conformity with the equation $$u_i = \int_{si} (n\nabla I^b) ds \quad (8)$$

$u_i$ is the direction derivative of the gradient $\nabla I^b$ along a path defined by two successive points of intersection (for example, V1, V2) on the same line candidate.

In order to reduce the calculation time, only those closed paths in which all segments of the closed path enclose a region of the source image in the counter-clockwise sense are examined. This region contains pixels with an X-ray intensity higher than that of the pixels outside this region. From the closed paths that are still feasible, that closed path along which the highest contrasts can be accumulated is selected as the shutter contour.

In order to avoid that the value $u_i$ is calculated several times for a path si which forms part of several closed paths, in the step 108 the values $u_i$ are calculated once in conformity with the equation 8 and taken up in an adjacency matrix. FIG. 5 shows such an adjacency matrix in which all corner points $V_1, V_2 \ldots V_9 \ldots$ must be entered. An entry is made only for corner points situated on the same line. In the row for $V_2$ there is an entry $u_{21}$ which relates to the path directed from $V_2$ to $V_1$. Analogously, there is an entry $u_{23}$ for the path directed from $V_2$ to $V_3$.

It would also be possible to make an entry for the path from $V_2$ to $V_4$ (as denoted by a cross in the row of $V_2$ and the column of $V_4$), but such an entry is not necessary. However, there is no entry for the path from $V_2$ to $V_5$, because $V_2$ and $V_5$ are not situated on one line. Moreover, there is no entry from $V_2$ to the points to the left of and below $V_2$, being situated on the same line as V2, because the path from V2 does not point in this direction (for the paths extending to V2 from such corner points which are not further indicated, however, an entry is made in the row for the relevant points and in the column for V2).

Therefore, in the step 109 the contour integral is calculated, in conformity with equation 7, from the entries for the paths of which the closed path is composed. This is repeated for all feasible paths enclosing a region in the counter-clockwise direction.

In the block 110 that closed path for which $U_{tot}$ is larger than that of all other closed paths is selected as the shutter contour. FIG. 4b shows the shutter contour thus found.

The shutter contour thus determined may be subjected to a plausibility test in the step 111 (however, because of the high reliability of this method, this step can also be dispensed with). The median value of the image values of the pixels in the region enclosed by the shutter contour is then formed. The number of pixels which are situated outside the region enclosed by the path and whose image value is larger than the median value thus calculated is then counted. The number of such apparently excessively bright pixels is divided by the number of pixels in the region enclosed by the shutter contour. If the number of "outliers" thus determined exceeds a given threshold value, for example 30%, the shutter contour found in the steps 101 to 110 is rejected again. Theoretically speaking, all pixels covered by the shutter should have an image value which is smaller than the median value in the region left uncovered by the shutter. Because of noise or artefacts of the image converter, however, there may be a number of "outliers" which have an image value higher than the median value. However, if this number becomes too large, it forms an indication that the shutter contour found has not been correctly determined. In this case the shutter contour found is replaced by the frame added in the step 102.

This completes the detection of the shutter contour (block 112).

A second possibility for determining the contrast accumulated along a closed path consists in calculating the surface integral $V_{tot}$ of the Laplacian operator in the region bounded by the closed path, said calculation being in conformity with:

$$V_{tot} = \int \Delta I^b da \quad (9)$$

Therein, $\Delta$ represents the Laplacian operator for which the symbol $\nabla^2$ is also customarily used The Laplacian operator $\Delta$ of a function f which is dependent on x and y is known to be calculated as $$\Delta f = \partial^2 f / \partial x^2 + \partial^2 f / \partial y^2 \quad (10)$$

Even though the formula for $V_{tot}$ according to the equation (9) at a first glance strongly deviates from the formula $U_{tot}$ according to the equation 6, it can be demonstrated by means of the divergence theorem that the two equations are mathematically identical.

Figure 8A:
Figure 8B:
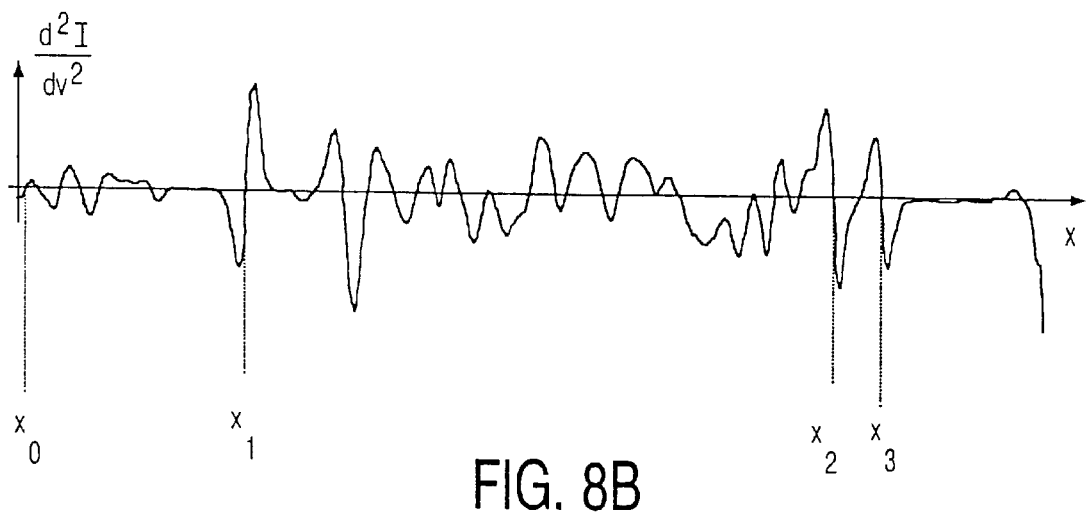

FIG. 8 shows a simplified version of the equation 9. FIG. 8a shows a typical variation of image values in the x direction and FIG. 8b shows the associated second derivative (representing the Laplacian operator for this one-dimensional case). Shutter edges appear in the form of particularly large values of the second derivative in the image shown in FIG. 8b, a positive value being compensated by a negative value of approximately the same magnitude. When the integral over the second derivative in the x direction is then formed between the zero-crossings $x_1$ and $x_2$, this integral (into which the integral of equation 9 changes for the one-dimensional case) is determined essentially by the positive amplitudes at $x_1$ and $x_2$. The parts of the curve situated therebetween essentially are averaged out. The second derivative, however, has further (relative) maxima and minima, for example, at $x_0$ and $x_3$. However, because they are values are smaller than those at $x_1$ and $x_2$, the integral over the second derivative would produce a smaller value from $x_0$ to $x_3$ than from $x_1$ to $x_2$.

Figure 7:
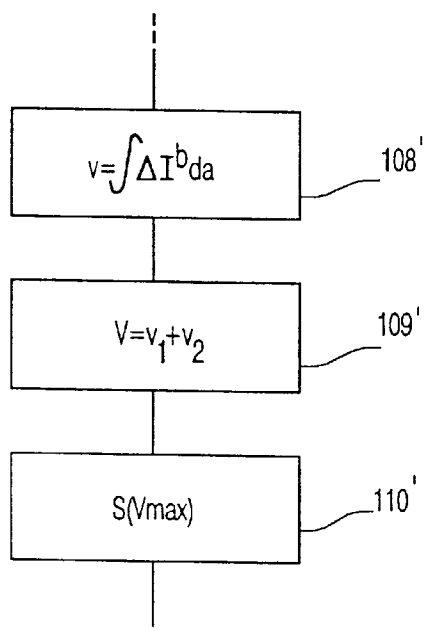
FIG. 7 shows a further version of the method shown in FIG. 2, FIGS. 8a and 8b show the variation of the image values on which the latter version is based.

On the basis of these considerations FIG. 7 shows a modified part of the flow chart of FIG. 2 which takes the place of the steps 108 to 110 therein.

In conformity with FIG. 4a all polygons feasible for the given situation of the corner points $V_1 \ldots V_9$ can be composed from one or more elementary polygons, some of which are denoted by the references $a_1 \ldots a_2 \ldots a_5$ in FIG. 4a. For each of these elementary polygons the surface integral over the Laplacian operator of the image values is calculated in conformity with the equation 9 in the step 108' so that, for example, for $a_1$ there is obtained a value $v_1$, and for $a_2$ a value $v_2$, etc. The Laplacian operator for each individual pixel can be derived from the gradients calculated in the step 103 by convoluting on the one hand the components $\nabla_x I$ in the neighboring pixels in this direction and in the x direction and on the other hand the components $\nabla_y I$ in the neighboring pixels in this direction and in the y direction with a kernel $-1, 0, +1$ and by adding the convolution products.

Every closed path encloses a polygon which is composed of one or more of such elementary polygons. Therefore, in the step 109' the associated values $v_1, v_2 \ldots v_5$ etc. are added for the elementary polygons ($a_1, a_2, a_5$ etc.) enclosed by the closed path, so that the total value $V_{tot}$ associated with the closed path is obtained.

In the step 110' from the closed paths thus evaluated that closed path for which the value $V_{tot}$ reaches a maximum is selected as the shutter contour. The shutter contour thus found can be subjected to a plausibility test again in conformity with step 111 in FIG. 2, before the method is terminated in block 112.

This method again offers possibilities for reducing the calculation time. This is because the larger the number of line candidates found, the larger the number of closed paths wherefrom the closed path representing the shutter contour must be selected will be. In the case of N line candidates, there are $2^N$ closed paths. In the case of very large values of N it is hardly possible to calculate the value $V_{tot}$ for each individual path.

Therefore, the path searched could be determined as follows while using significantly fewer calculations. Starting from a vector having as many components as there are line candidates (N), a vector component is assigned to each line candidate, said component having a value providing information as to whether this line candidate forms part of the shutter contour (in which case the component has the value 1) or not (in which case the value of the component is 0). Starting from a start vector for which, for example all components are set to 0, it is checked for which individual line candidates the maximum value $V_{tot}$ is obtained (to this end, the values $v_1, V_2 \ldots$ etc. must be added for all elementary polygons $a_1, a_2$ etc., which are situated to the left of this line candidate, viewed in a direction of the arrow associated with the line candidate). The line candidate for which the largest value $V_{tot}$ is obtained is inverted (set from 0 to 1 or from 1 to 0). Subsequently, the method is repeated in that the vector components are inverted for all line candidates while it is tested which single inversion leads to the largest value $V_{tot}$. This is repeated until the surface integral over the Laplacian operator ($V_{tot}$) no longer increases.

Figure 9:
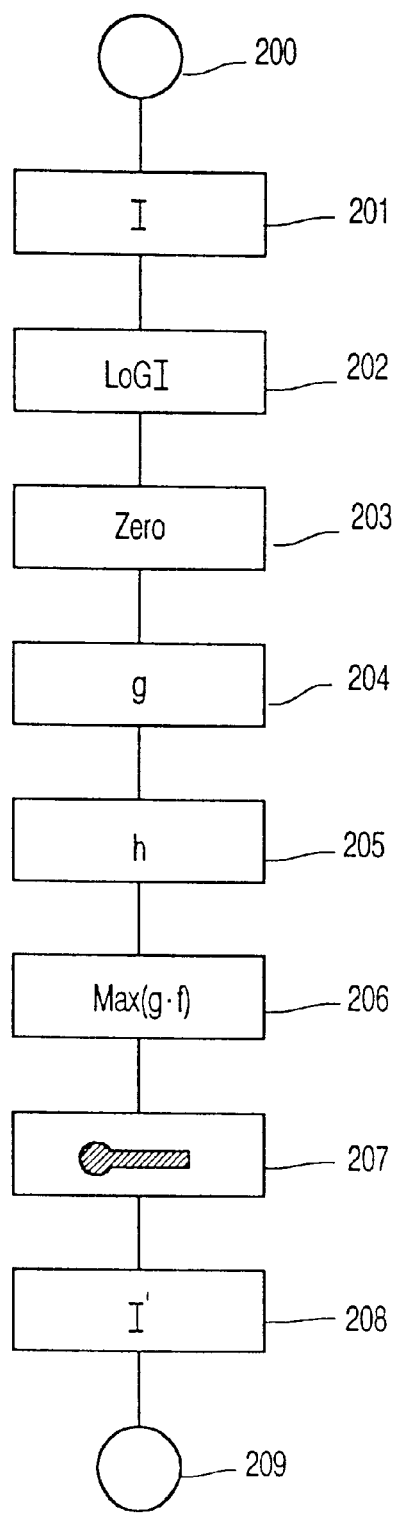
FIG. 9 shows a flow chart for the automatic detection of an implant contour in the X-ray image.

A method for the automatic detection of the contour of an implant will be described in detail hereinafter with reference to the flow chart shown in FIG. 9.

After the initialization in the block 200, first the X-ray image is prepared in the step 201 as described in detail for the step 101 of the flow chart of FIG. 2. This yields an image with image values I which are a function of the location x,y.

In the step 202 a so-called LG filter (LoG=Laplacian of Gaussian) is applied to the image I thus prepared. The LoG filter is a known image processing filter which forms the second spatial derivative of the image values after smoothing by means of a Gaussian low-pass filter in conformity with the relation:

$$I_{LoG} = \Delta I^b(x, y)\exp(-(x^2+y^2)/2\sigma^2) \quad (11)$$

where $I_{LoG}$ represents the image values thus filtered and $\sigma$ is a parameter which represents the width of the Gaussian low-pass filtering. Such filtering can be suitably approximated by subtraction of two Gaussian filtering operations with a different kernel size (DoG filter=Difference of Gaussians). A contour in the X-ray image corresponds to a zero-crossing in the LoG filtered image. (The change of sign is shown as the zero-crossing). The contour lines obtained when following the zero-crossings in the LoG filtered image have the known property that they are always closed. Starting from an arbitrary pixel in which such a zero-crossing occurs, this pixel is reached again when the successive zero-crossings are followed. It is a further known property of the LoG filtered image that the resultant closed paths never intersect. In the step 203 the contours can thus be detected in the source image or the X-ray image.

This method is simpler than in the case where contour points are determined first, subsequently lines connecting these contour points are determined and finally closed paths are composed from the lines, one of said paths representing the contour searched. However, it is not advisable to use this method for the automatic detection of shutter contours, because the shutter contour in an X-ray image often has sections which are very difficult to identify due to of their low contrast and because the zero-crossings can no longer be followed in such a case.

From among the contours thus found that contour which most probably represents an implant must be selected. For the determination of this contour it is assumed that it has a mean contrast value which is higher than that of the other contours and that it, moreover, has a higher degree of straightness than contours of anatomical objects. In this respect it is assumed that an artificial implant in the X-ray image has a straighter, but at least a smoother contour than a natural structure.

Consequently, in the step 204 the mean contrast is determined and in the step 205 a measure of straightness of the contour. The contrast g can be determined in conformity with the following equation:

$$g = \frac{i_{out} - i_{in}}{i_{out} + i_{in}} \quad (12)$$

Therein, $i_{in}$ is the mean value of the image values on the inner side of the contour and $i_{out}$ is the mean value of the image values on the outer side of the contour. Another possibility consists in calculating the values $U_{tot}$ in conformity with the equation 6 and $V_{tot}$ in conformity with the equation 9, and in dividing these values by the length of the contour.

Figure 10:
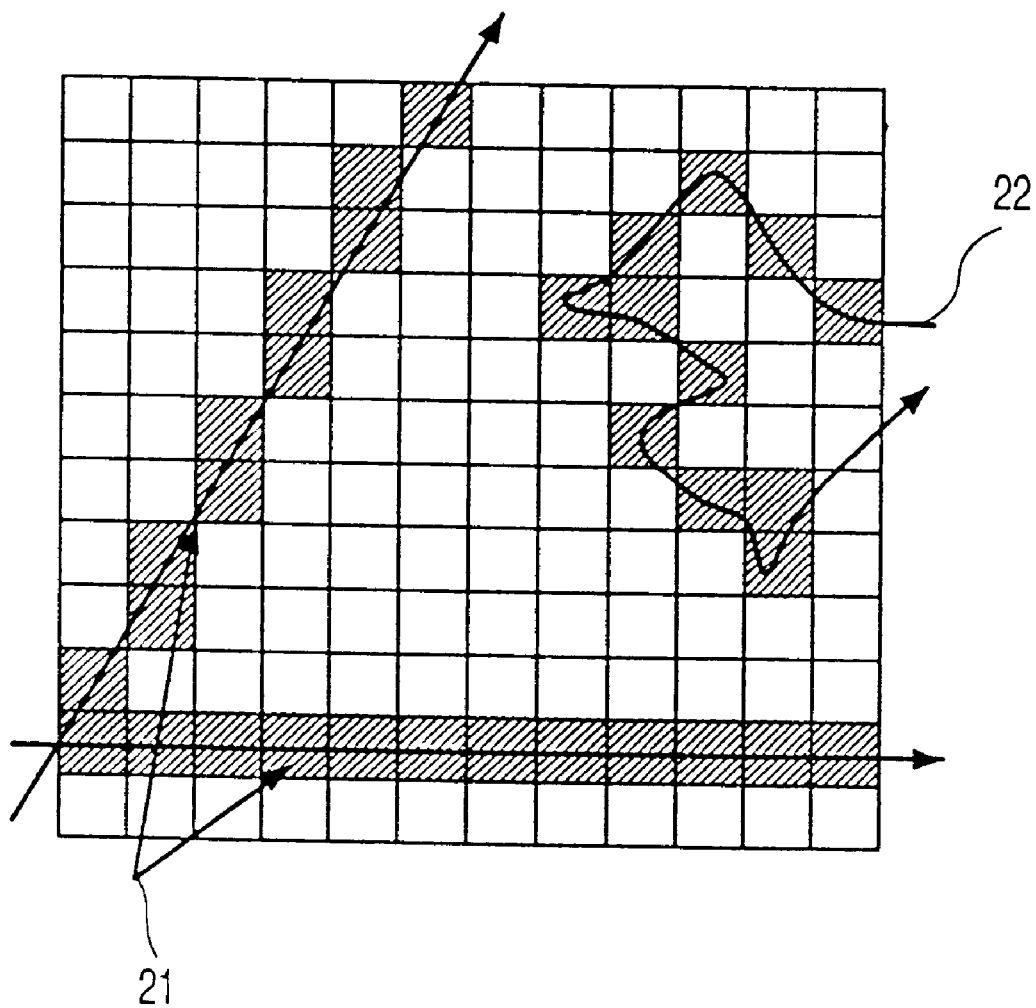
FIG. 10 shows an image region with straight and curved segments.

For each pixel $P_i$ on the contour a measure of straightness $h_i$ is calculated from the co-ordinates of N neighboring pixels on the contour in conformity with the relation:

$$h_i = d/N,$$

in which d is the maximum from the distances dx, dy between the first one of these pixels in the x and the y direction from the last of the N pixels. FIG. 10 illustrates the significance of this measure. Therein, two contours 21 are shown which are straight at least over a given number of pixels. The distance dx between the first and the last pixel on the horizontal contour, measured in pixel widths, corresponds to the number N of pixels, so that in this case the measure hi assumes the value 1. For the sloping straight line the distance d (in this case d=dy) is slightly smaller, so that the value $h_i$ is also smaller, but it is still larger than 0.7. For the curved contour 22, however, d (in this case d again equals dy) amounts to only 2 (pixel widths), so that a smaller value is obtained for $h_i$.

The straightness measure h for the overall contour is the mean value of the measures $h_i$ in the individual pixels of the contour. The straightness measure h or $h_i$ can be adapted to the requirements by way of the number N of pixels taken into account for the calculation of $h_i$. The smaller the number N, the more the value $h_i$ will increase in the case of an arcuate curve. Therefore, a smooth, uniformly curved contour is also evaluated as being straight when the length defined by N successive pixels is small in comparison with the radius of curvature of this contour.

In the step 206 that contour is selected for which the product of the values of g and h, determined in the steps 204 and 205, is maximum. This contour represents the searched contour of the implant. In the step 207 the region enclosed by the contour found for the implant is eliminated and in the step 208 the parameters for the automatic adjustment of the contrasts on a monitor (or in a hardcopy unit) are determined in known manner from the residual image, thus enabling the X-ray image to be reproduced with optimum contrast.

All references cited herein, as well as the priority documents German Patent Applications 19911587.7 and 19916821.0 filed Mar. 16, 1999 and Apr. 14, 1999, respectively, are incorporated herein by reference in their entirety and for all purposes to the same extent as if each individual publication or patent or patent application was specifically and individually indicated to be incorporated by reference in its entirety for all purposes.

What is claimed is:

1. A method for automatically detecting contours of structures having a high X-ray absorption in an X-ray image comprising:

determining a number of closed paths which serve as contour candidates in an X-ray image or an image derived therefrom, and selecting, in dependence on the contrasts along the closed paths, the contour as a closed path from the number of closed paths.

2. A method as claimed in claim 1 wherein the structures having a high X-ray absorption comprise a shutter, and wherein the step of determining the closed paths further comprises:

determining contour point candidates from the spatial variation of the image values associated with the pixels of the X-ray image or a source image derived therefrom, determining line candidates from the contour point candidates in such a manner that a row of contour point candidates is situated on each line candidate or immediately adjacent to such a candidate, and forming closed paths as shutter contour candidates composed of segments of different line candidates.

3. A method as claimed in claim 1 wherein the structures having a high X-ray absorption comprise an implant, and wherein the step of determining the closed paths further comprises:

application of a Laplacian-of-Gaussian filter to an X-ray image or an image derived therefrom, and determination of the closed paths on which the zero-crossings of the Laplacian-of-Gaussian-filtered image are situated.

4. A method as claimed in claim 2, wherein the step of selecting further comprises summing the contrasts at the edges to both sides of one of several closed paths, and determining the closed path along which the sum is maximum as the shutter contour.

5. A method as claimed in claim 4 wherein the step of summing the contrasts further comprises forming the contour integral ($U_{tot}$) along the closed path (s) of the direction derivative of the gradient ($\nabla I$) of the image values (I) in the direction of the path (s) in conformity with:

$$U_{tot}=\oint(n\nabla I^a)ds,$$

where n is a unit vector perpendicular to the closed path (s) and a is an exponent greater than or equal to 1.

6. A method as claimed in claim 4 wherein the step of summing the contrasts further comprises forming the integral ($V_{tot}$) of the Laplacian operator ($\Delta$) of the image values in the region (a) enclosed by the closed path in conformity with:

$$V_{tot}=\int \Delta I^b da.$$

7. A method as claimed in claim 2 wherein the step of selecting is restricted to closed paths which enclose a respective region within which the image values are larger than those outside this region.

8. A method as claimed in claim 2 wherein those points in the X-ray image or in the source image in which the image values exhibit the largest gradients are determined as contour point candidates.

9. A method as claimed in claim 2 wherein the line candidates are determined from the contour point candidates by a Hough transformation.

10. A method as claimed in claim 2 further comprising adjusting a frame around the source image, the pixels in this frame corresponding to the image values in the region masked by shutters.

11. A method as claimed in claim 1 wherein the structures having a high X-ray absorption comprise an implant, and wherein a closed path is automatically selected, from the number of closed paths, as an implant contour in dependence on a straightness measure evaluating the straightness of the closed paths.

12. A method as claimed in claim 11 wherein in order to determine the straightness measure, the distance between the first pixel and the last pixel in a segment of a closed path which includes a number of neighboring pixels is determined in relation to the length of this segment.

13. A method as claimed in claim 1 further comprising automatic contrast adjustment in dependence on the content of the X-ray image during which the region enclosed by the implant contour is suppressed.

14. An X-ray apparatus comprising:

an X-ray source for generating X-rays which traverse an examination zone, a shutter device which is arranged between the X-ray source and the examination zone, an X-ray image converter for detecting the X-rays behind the examination zone and for generating a corresponding source image, and an image processing unit for the detection of the contours of the shutter device in the source image, wherein the image processing unit is arranged to carry out a processing method comprising the steps of:

determining contour point candidates from the spatial variation of the image values associated with the pixels of the X-ray image or a source image derived therefrom, determining line candidates from the contour point candidates in such a manner that a row of contour point candidates is situated on each line candidate or immediately adjacent to such a candidate, forming a number of closed paths as shutter contour candidates composed of segments of different line candidates, and selecting a closed path, from the number of closed paths, as the shutter contour in dependence on the contrasts to both sides of the closed paths.

* * * * *